United States Patent [19]

Olsen et al.

[11] Patent Number: 5,112,308
[45] Date of Patent: May 12, 1992

[54] MEDICAL DEVICE FOR AND A METHOD OF ENDOSCOPIC SURGERY

[75] Inventors: Douglas O. Olsen, Brentwood, Tenn.; Brian L. Bates; Thomas A. Osborne, both of Bloomington, Ind.

[73] Assignee: Cook Incorporated, Bloomington, Ind.

[21] Appl. No.: 592,676

[22] Filed: Oct. 3, 1990

[51] Int. Cl.⁵ .......................... A61M 5/178
[52] U.S. Cl. ................. 604/164; 604/104; 604/265; 604/167
[58] Field of Search .......... 604/158, 160, 161, 164, 604/169, 170, 166, 264, 265, 167, 171, 104, 280; 128/772, 4, 6, 5

[56] References Cited

U.S. PATENT DOCUMENTS

| | | | |
|---|---|---|---|
| 3,313,299 | 4/1967 | Spademan | 604/167 |
| 4,096,860 | 6/1978 | McLauglin | 604/167 |
| 4,261,357 | 4/1981 | Kontos | 604/169 |
| 4,581,019 | 4/1986 | Curelaru et al. | 604/164 |
| 4,629,450 | 12/1986 | Suzuki et al. | 604/104 |
| 4,729,914 | 3/1988 | Kliment et al. | 604/264 |
| 4,862,891 | 9/1989 | Smith | 128/343 |
| 4,935,008 | 6/1990 | Lewis, Jr. | 604/164 |
| 4,950,257 | 8/1990 | Hibbs et al. | 604/265 |
| 4,954,130 | 9/1990 | Edwards | 604/169 |
| 4,981,482 | 1/1991 | Ichikawa | 604/104 |
| 5,041,097 | 8/1991 | Johnson | 604/264 |

OTHER PUBLICATIONS

"Suprapubic Balloon Cannula Set," Percutaneous Catheters and Sets. Cook Urological Incorporated Surgical Products Catalog. 1990-1991, p. 124.

Primary Examiner—Cary E. O'Connor
Attorney, Agent, or Firm—Richard J. Godlewski

[57] ABSTRACT

A medical device for endoscopic access of a body cavity and a method of percutaneously placing inner and outer access sheaths of the device into the body cavity. The medical device includes inner and outer access sheaths and a dilator which is inserted into the outer sheath and has a shoulder or a shoulder piece for abutting against the proximal end of the outer sheath. The device also includes a wire guide that is percutaneously inserted into the body cavity via an introducer needle. The dilator and outer sheath are placed over the wire guide to dilate the puncture site and introduce the dilator and outer sheath into the body cavity. The dilator comprises an elongated cylindrical member having a passageway opening distally from the conically-shaped distal end and from an outside lateral wall of the dilator about the proximal end. The dilator also includes an end cap which is utilized to force the dilator and the outer sheath through the puncture site and into the body cavity. After positioning in the body cavity, the dilator and wire guide are removed through the outer sheath. The inner sheath is then inserted through the outer sheath into the body cavity. The proximal ends of both the inner and outer sheaths include seals for maintaining insufflation of the body cavity. The inner sheath includes a shoulder piece having a chamber and a side port for connection to an insufflation gas line.

25 Claims, 5 Drawing Sheets

MEDICAL DEVICE FOR AND A METHOD OF ENDOSCOPIC SURGERY

TECHNICAL FIELD

This invention relates to medical devices for performing endoscopic surgery and, in particular, a medical device and method of percutaneously accessing a body cavity for an endoscopic surgical procedure.

BACKGROUND OF THE INVENTION

Gallstones are a common problem in the United States and the most frequent cause of gallbladder inflammation. About 500,000 cholecystectomies are performed each year with an overall medical cost nearing approximately two billion dollars. Patients of all ages with cholecystitis have a mortality rate of 1.3% to 5%. For those over 65 years of age, the rate increases to 10%. When empyema of the gallbladder is present, the mortality rate is close to 29%. As the population ages, there will be more poor-risk patients with troublesome gallstones.

Removal of only gallstones, without a cholecystectomy, offers promise of reducing risks, but only solves the problem temporarily. Nearly 50% of the patients having a surgical cholecystectomy with the gallbladder left intact, will have a recurrence of gallstones within three years or less and 80% will develop stones within 15 years.

Calculi in other parts of the biliary system are also commonplace as are calculi in the urinary system. Several percutaneous and open surgical procedures are available for removing calculi from the biliary or the urinary system. With respect to the biliary system, one invasive, open surgical procedure is the cholecystectomy in which the gallbladder is removed along with stones from the common duct. In addition, a T-tube is commonly inserted in the duct for removal of residual calculi. However, this procedure is, as are other open surgical procedures, subject to an extensive recovery period lasting anywhere from two to six or more weeks.

Minimally invasive endoscopic procedures that utilize percutaneous access sheaths include a percutaneous cholecystectomy in which the gallbladder is removed along with any stones from the common duct and a percutaneous cholelithotomy in which calculi are removed from the gallbladder.

One prior art percutaneous trocar access sheath includes a three-sided, pointed end trocar surrounded with an access sheath. The access sheath has a distal tip that slides back or retracts to expose the three-sided, pointed end trocar for puncturing the abdominal wall including the facia and for entering the peritoneal cavity. The retractable distal end of the access sheath includes a spring-loaded mechanism for sliding the distal tip of the access sheath over the pointed end of the trocar after the trocar pierces the abdominal wall. The fully extended distal tip of the access sheath covers the pointed end of the trocar after insertion into the peritoneal body cavity to prevent the pointed end trocar from perforating the bowel or any other organs or tissue within the peritoneal cavity. However, the time delay associated with the distal tip sliding forward to cover the pointed end of the trocar permits the surgeon to perforate or puncture any of the organs or tissue in the peritoneal cavity particularly after the sudden surge associated with puncturing the abdominal wall.

Another disadvantage of the three-sided, pointed end trocar and sheath is that the pointed end cuts tissue as it passes through the abdominal wall, causing undesired trauma and producing a three-slit puncture site which is difficult to suture upon completion of the surgery.

SUMMARY OF THE INVENTION

The foregoing and other problems are solved and a technical advance is achieved by an illustrative medical, endoscopic access device for percutaneously accessing a body cavity such as the peritoneal cavity during, for example, a percutaneous cholecystectomy surgical procedure. The access device advantageously comprises a dilator including an elongated member having a tapered distal end for dilating rather than cutting the puncture site leading into the peritoneal cavity. The surgeon typically utilizes an introducer needle to access and insufflate the peritoneal cavity via the umbilicus. A wire guide is introduced through the needle, and the needle is removed, leaving the guide in place. The dilator advantageously includes a hollow passageway extending longitudinally in the elongated member and opening from the tapered distal end and from an outside lateral wall of the elongated member. The physician inserts the dilator over the wire guide which exits from the lateral wall opening. An end cap is attached and extends from the proximal end of the elongated member to permit the physician to push and introduce the dilator into the puncture site and the peritoneal cavity. The dilator advantageously dilates the puncture site rather than cutting it as with the three-sided, pointed end trocar.

The tapered distal end of the elongated dilator member is coated with a hydrophilic material which when wetted facilitates the dilation of and entry into the peritoneal cavity.

The endoscopic access device also includes an outer sheath having a passageway extending longitudinally therethrough and sized for positioning the elongated dilator member therein. The distal end of the outer sheath is tapered to permit further dilation of the puncture site and entry into the peritoneal cavity. Attached to the proximal end of the outer sheath is a fitting including a flexible seal having an aperture communicating with the passageway and sized for sealing against the outside lateral wall of the elongated member when the member is inserted through the aperture.

The elongated member further includes a shoulder positioned by the proximal end and sized for abutting against the proximal end of the outer sheath to force the sheath through the puncture site when the surgeon exerts force on the end cap of the dilator. The dilator passageway opens laterally from the shoulder to permit the wire guide to pass therefrom and not interfere with the surgeon's introduction of the access device. Advantageously, the outer sheath also includes a material having a slick surface for ease of passage through the puncture site.

After the dilator member and outer sheath are introduced into the peritoneal cavity through the puncture site, the dilator member is removed along with the wire guide from the peritoneal cavity via the outer sheath. The medical device further comprises an inner sheath including a distal end, a proximal end, and a passageway extending longitudinally therebetween. The inner sheath is sized for positioning within the passageway of the outer sheath and also includes a shoulder positioned about the proximal end thereof and sized for abutting against the proximal end of the outer sheath. The shoulder of the inner sheath includes a side port communicating with the passageway thereof and extending laterally therefrom for connection to an insufflating gas line. Attached about the proximal end of the inner sheath is a flexible seal having a slit for inserting endoscopic surgical instruments therethrough and sealing around them. The inner sheath also comprises a second flexible seal attached about the proximal end having an aperture positioned adjacent to the slit for further facilitating access and positioning of endoscopic surgical instruments.

With respect to one aspect of the medical device, the elongated dilator member comprises a thermoplastic material that is formed or molded into the elongated member with the hollow passageway extending therein and opening from the conically-shaped tapered distal end distally and from the outside lateral wall about the proximal end. The end cap is also formed therewith to extend from the proximal end of the elongated member.

With respect to another aspect of the medical device, a dilator comprises a first outer elongated member having a conically-tapered distal end with a first hollow passageway extending longitudinally therein. A second elongated member is positioned within the first passageway and also has a passageway which opens from the tapered distal end of the first member and from the outside lateral wall about the proximal end of the first member. An end cap is attached and extends from the proximal end of the first elongated member. A sleeve is attached about the proximal end of the first member and to the end cap and has a lateral opening communicating with the passageway of the second member to permit a wire guide to extend therethrough. The first member also includes a hydrophilic material coating the distal end to further facilitate dilation of the puncture site and entry of the dilator member into the peritoneal cavity. The device also includes a wire guide sized for passing through the passageway of the inner elongated member.

The method of percutaneously placing inner and outer access sheaths into a body cavity such as the peritoneal cavity includes introducing the wire guide percutaneously into the body cavity via an introducer needle inserted at the puncture site. A dilator is inserted into the outer sheath and placed over the wire guide. The procedure further includes dilating the puncture site with the dilator and outer sheath placed over the wire guide. The dilator and outer sheath are positioned into the body cavity over the wire guide with the surgeon exerting force on the end cap positioned at the proximal end of the dilator. To further facilitate dilation of the puncture site, a hydrophilic material coating the conically-shaped distal end of the dilator is wetted and force is applied to the end cap at the proximal end of the dilator to introduce the wetted distal end of the dilator into the puncture site. When the dilator and outer sheath are introduced into the body cavity, the dilator and wire guide are removed from the body cavity through the outer sheath, and the inner sheath is introduced into the body cavity through the outer sheath. Continued insufflation of the body cavity is maintained through the side port of the inner access sheath positioned about the proximal end of the inner sheath.

DETAILED DESCRIPTION

Figure 1:
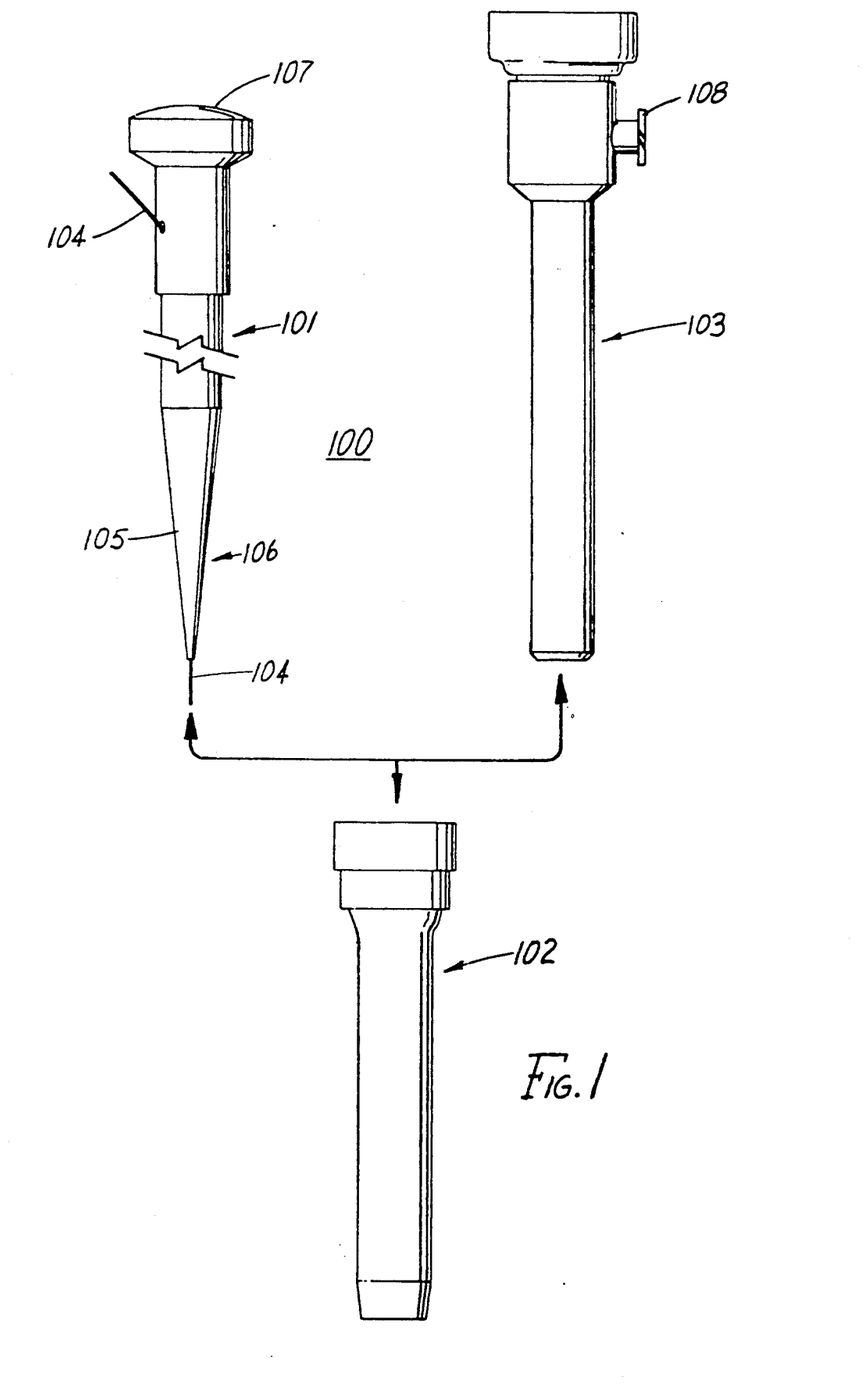
FIG. 1 depicts the medical device of the present invention.

Depicted in FIG. 1 is a preferred illustrative embodiment of medical device 100 for percutaneously accessing a body cavity for an endoscopic surgical procedure. The medical access device comprises dilator 101, outer sheath 102, and inner sheath 103. Dilator 101 is positioned in the hollow passageway of outer sheath 102 and percutaneously inserted into a body cavity via wire guide 104. By way of example, the surgeon introduces an introducer needle into the peritoneal body cavity via the umbilicus. The peritoneal cavity is typically insufflated with a gas such as carbon dioxide, and the wire guide 104 is inserted into the insufflated body cavity via the puncture site formed by the introducer needle. Dilator 101 is inserted into outer sheath 102 and placed over wire guide 104. The puncture site is dilated, and the dilator and outer sheath are introduced into the insufflated peritoneal cavity by applying a force to end cap 107 of the dilator. The dilation of the puncture site is enhanced by first wetting hydrophilic material 105 coating the conically-shaped distal end 106 of the dilator. The dilator and wire guide are removed through the outer sheath positioned in the body cavity, and the inner sheath 103 is positioned in the passageway of the outer sheath. Insufflation of the body cavity is maintained through side port 108 laterally positioned about the proximal end of the inner access sheath.

Figure 2:
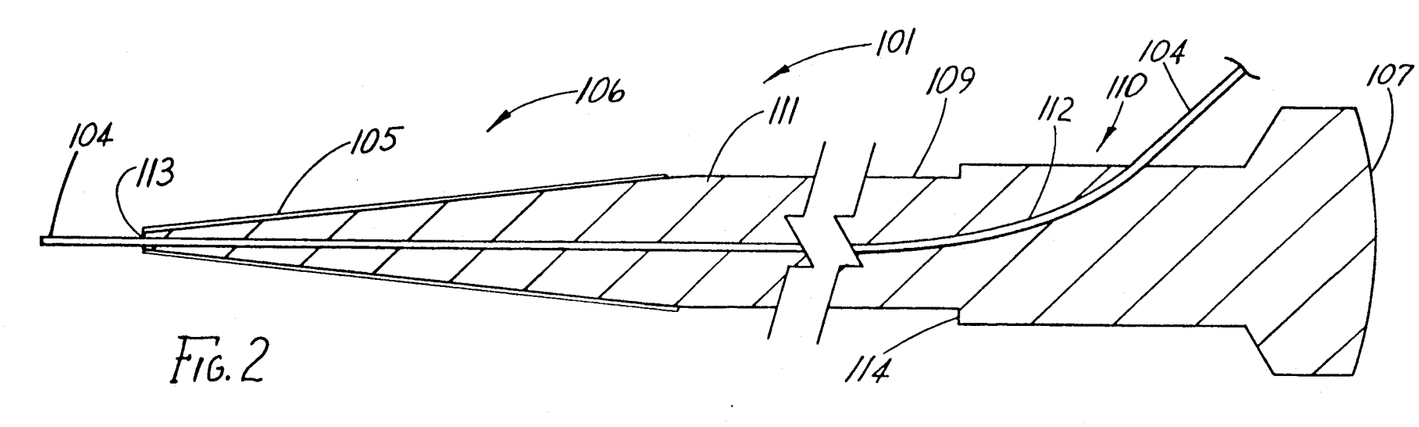
FIG. 2 depicts a cross-sectional view of one aspect of the dilator and wire guide of FIG. 1.

Depicted in FIG. 2 is a cross-sectional view of dilator 101 with wire guide 104 extending through passageway 112. Dilator 101 comprises an elongated member 109 having a conically-tapered distal end 106, proximal end 110, and outside lateral wall 111 extending between the two ends. Hollow passageway 112 extends longitudinally in the elongated member and opens distally from the tapered distal end at opening 113 and laterally from the outside lateral wall about the proximal end. Passageway 112 is sized for extending wire guide 104 therethrough as shown. End cap 107 is positioned at and extends from proximal end 110 of the elongated member. This end cap fits easily into the palm of the surgeon's hand or is easily grasped by the fingers to apply force to the dilator for introducing the tapered distal end into the puncture site over wire guide 104. The dilator also includes a well-known hydrophilic material 105 coating the tapered distal end, which is wetted with, for example, saline to ease dilation of the puncture site. The elongated member further includes shoulder 114 positioned about the proximal end of the elongated member, which is sized for abutting against the proximal end of outer sheath 102. Shoulder 114 fixedly positions the dilator against the proximal end of outer sheath 102 when the dilator and outer sheath are being introduced into the peritoneal body cavity via the puncture site.

Figure 3:
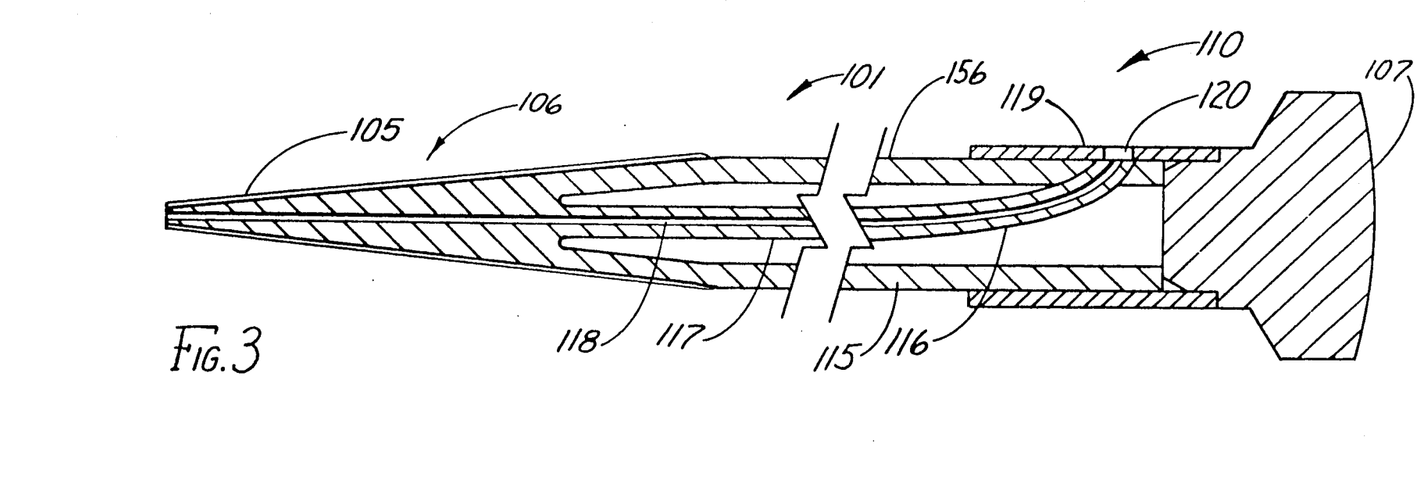
FIG. 3 depicts a cross-sectional view of another aspect of the dilator of FIG. 1.

Depicted in FIG. 3 is another aspect of dilator 101 including a first elongated member 156 having conically-tapered distal end 106, proximal end 110, and side lateral wall 115 extending between the two ends. Hollow passageway 116 extends longitudinally between ends 106 and 110. The dilator further includes a second elongated member 117 positioned within passageway 116 and having a passageway 118 opening from conically-tapered distal end 106 distally and from side lateral wall 115 laterally about proximal end 110. End cap 107 is attached and extends from the proximal end of first elongated member 156 via sleeve 119. Sleeve 119 is attached about the proximal end 110 of the first member and to the end cap and has a lateral opening 120 communicating with the passageway of elongated member 117.

First and second elongated members 156 and 117 are comprised of a well-known rigid, thermoplastic material such as polyvinylchloride having a durometer of approximately 90 on the Shore A scale. Elongated member 156 comprises a 38 French polyvinylchloride tube approximately 25 cm in length. Second member tube 117 comprises a 28 French polyvinylchloride tube also approximately 25 cm in length. The second member tube is inserted in passageway 116 of the first member tube with a mandril inserted into passageway 118 of the second tube. The two distal ends are heated to melt the two distal ends together to form conically-tapered distal end 106 approximately 5 cm in length. The proximal end of the inner member tube is glued to the outside lateral wall about the proximal end of the outer member tube. Polyvinylchloride sleeve 119 is placed over the proximal end of the outer member tube attached thereto using a well-known medical grade adhesive. Opening 120 is formed in the sleeve to permit communication with passage 118 of the inner member tube. The opening and inner member passageway are large enough to permit a commercially available wire guide having, for example, a 0.038"outer diameter to pass readily therethrough. End cap 107 is a circular knob having an outer diameter of approximately 25 mm and a length of approximately the same dimension which is inserted into the opening of the sleeve and attached thereto using again, for example, medical grade adhesive. A well-known hydrophilic material 105 coats the conically-tapered distal end of the dilator.

The dilator depicted in FIG. 2 is comprised of, for example, the same thermoplastic polyvinylchloride material having approximately the same dimensions as the dilator of FIG. 3.

Figure 4:
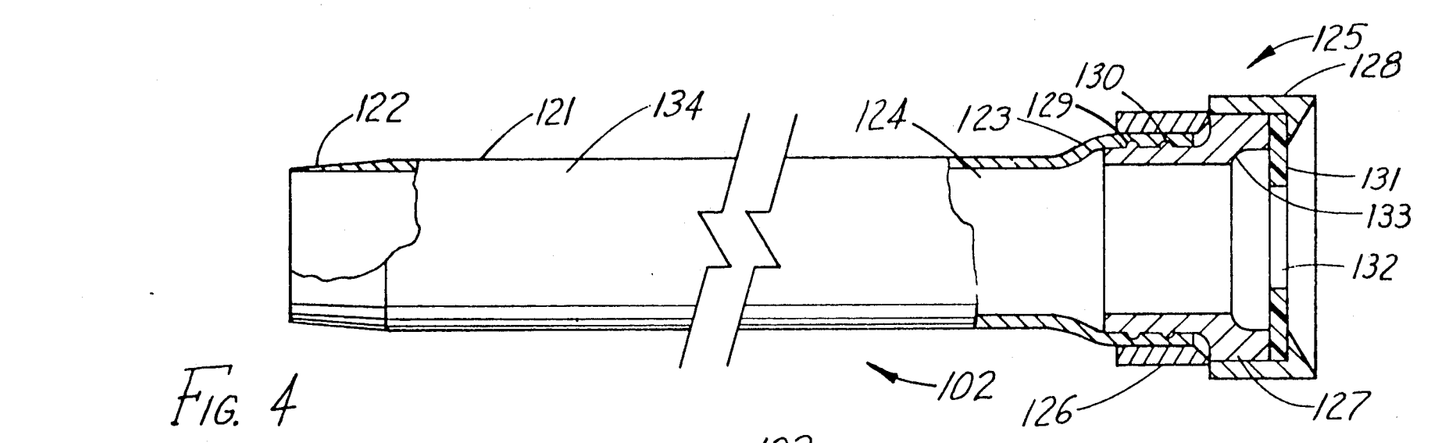
FIG. 4 depicts a partial cross-sectional view of the outer access sheath of FIG. 1.

Depicted in FIG. 4 is outer sheath 102 of FIG. 1. Outer sheath 102 comprises a well-known thermoplastic material tube 121 such as polytetrafluoroethylene having a slick outer surface. This thermoplastic material is also a rigid thermoplastic having a durometer of approximately 90 on the Shore A scale. Tube 121 has a tapered distal end 122, a flared proximal end 123 at the opposite ends of passageway 124 extending longitudinally through the tube. The outer sheath tube is approximately 15 cm in length and has an inner diameter of 38 French to position dilator 101 therethrough. Fitting 125 is attached to proximal end 123 of the outer sheath tube. Fitting 125 is comprised of three acetal polymer components 126, 127, and 128. Circular T-shaped sleeve 127 with annular rings 129 and 130 is pushed into flared proximal end 123. Lock ring 126 is press-fitted over the outside of flared proximal end 123 to attach fitting 125 to inner sheath tubing 121. Beveled annular end cap 128 is positioned as shown to fit over the T-shaped sleeve 127 to position silicon material seal 131 therebetween. Well-known medical grade adhesive affixes beveled end cap 128 to T-shaped sleeve 127. Silicon material seal 131 has an approximate 9 mm aperture 132 therein which seals against the outside lateral wall of dilator 101 when the dilator is inserted into passageway 124 of the outer sheath. When inserted therein, the proximal end of sleeve 119 engages the silicon seal and abuts against edge 133 of the T-shaped sleeve 127. This fixedly positions the outer sleeve with respect to dilator 101. Likewise shoulder 114 also abuts against seal 131 and passage 133 of the T-shaped sleeve, again to affix the relative position of the dilator with respect to the outer sheath. The polytetrafluoroethylene material of the outer sleeve tube has a slick surface 134 for engaging and sliding through the dilated puncture site when distal end 122 comes in contact therewith.

Figure 5:
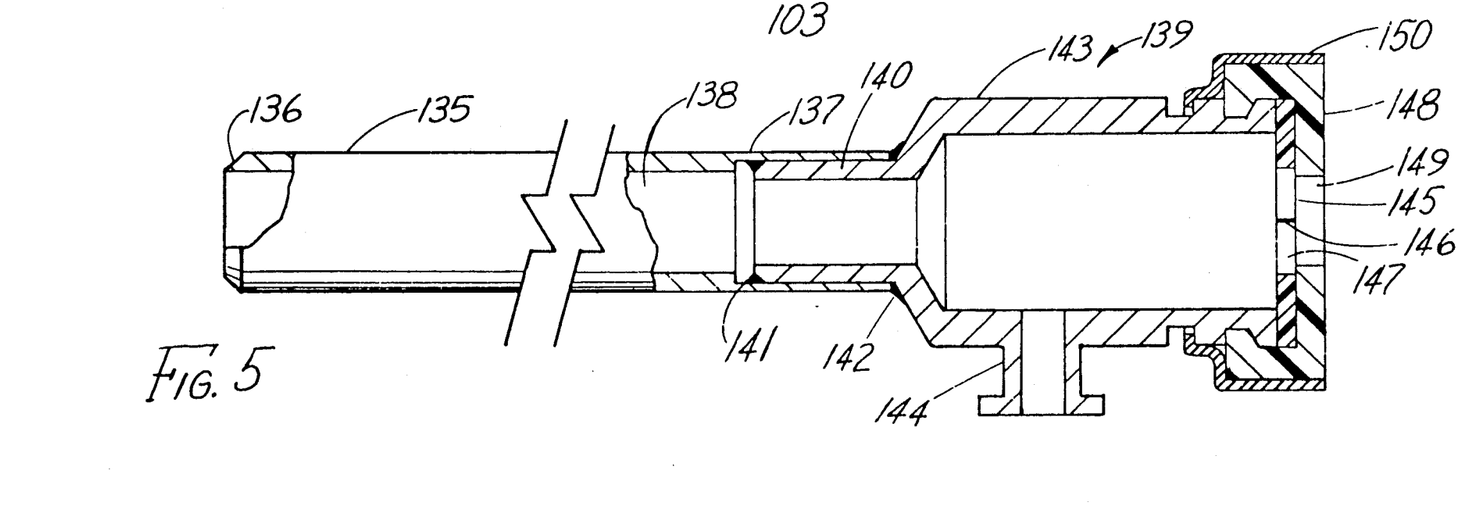
FIG. 5 depicts a partial view of the inner access sheath of FIG. 1.

Depicted in FIG. 5 is inner sheath 103 of FIG. 1. The inner sheath is approximately 15 cm in overall length and comprises an optically clear, very rigid thermoplastic material tube 135 having an extremely high durometer. Such a thermoplastic material is cellulose acetate butyrate. Inner sheath tube 135 is approximately 15.5 cm in length and has an outer diameter of 0.497" and an inner diameter of 0.426". The inner sheath tube has a tapered distal end 136 and a proximal end 137 at opposite ends of hollow passageway 138 extending longitudinally in the tube. The sheath is sized for positioning within the passageway of outer sheath 102 and has a hollow passageway sized to permit the use of endoscopic instruments up to 10 mm in diameter. The inner sheath also includes shoulder piece 139 having a distal neck 140 that is positioned into the proximal end 137 of the inner sheath tube. Medical grade adhesive 141 and 142 are utilized to cement the two pieces together. The larger diameter shoulder 143 is positioned about the proximal end of the inner sheath and is sized for abutting against the proximal end of the outer sheath. Passageway 138 extends through shoulder piece 139. Side port 144 laterally extends from the shoulder piece and communicates with passageway 138. The port is flanged for securing a Luer lock fitting of an insufflating line thereto. First seal 145 is positioned at the proximal end of the shoulder piece and includes criss-crossed slits 146 and 147 for permitting passage of endoscopic instruments therethrough and forming a seal thereabout. These slits communicate with passageway 138 of the inner sheath. The second flexible seal 148 is also attached about the proximal end of the shoulder piece and has an aperture 149 formed therein adjacent to the criss-crossed slits for positioning endoscopic instruments placed therethrough. The aperture is positioned against the slits to further facilitate a gas-tight seal against endoscopic instruments inserted therethrough. The second seal is attached to the proximal end of the shoulder piece with a polyethylene shrink tube 150 as shown.

Figures 6, 7:
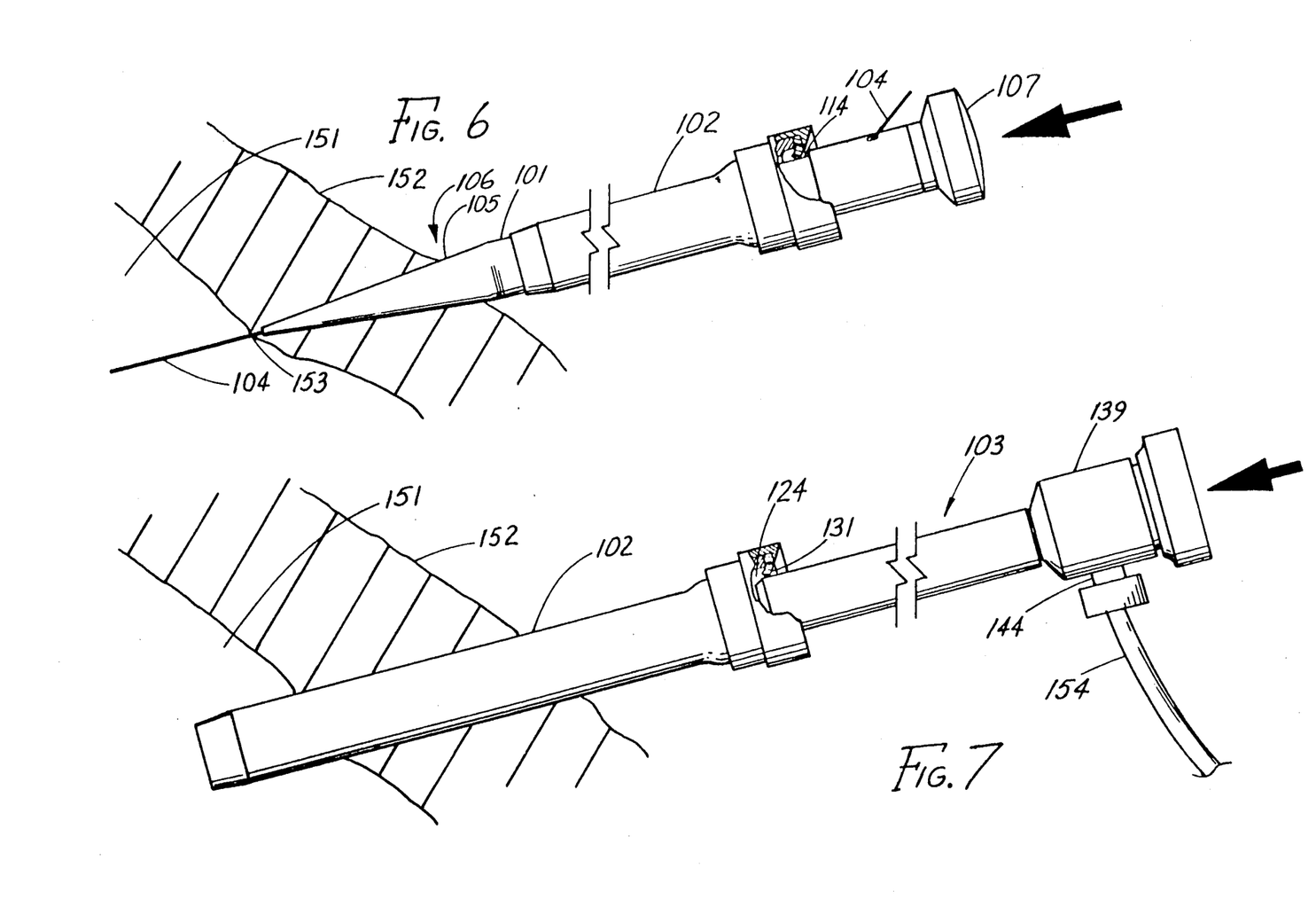
FIGS. 6-8 depict the method of percutaneously placing the inner and outer access sheaths of FIG. 1 into a body cavity.
Figure 8:
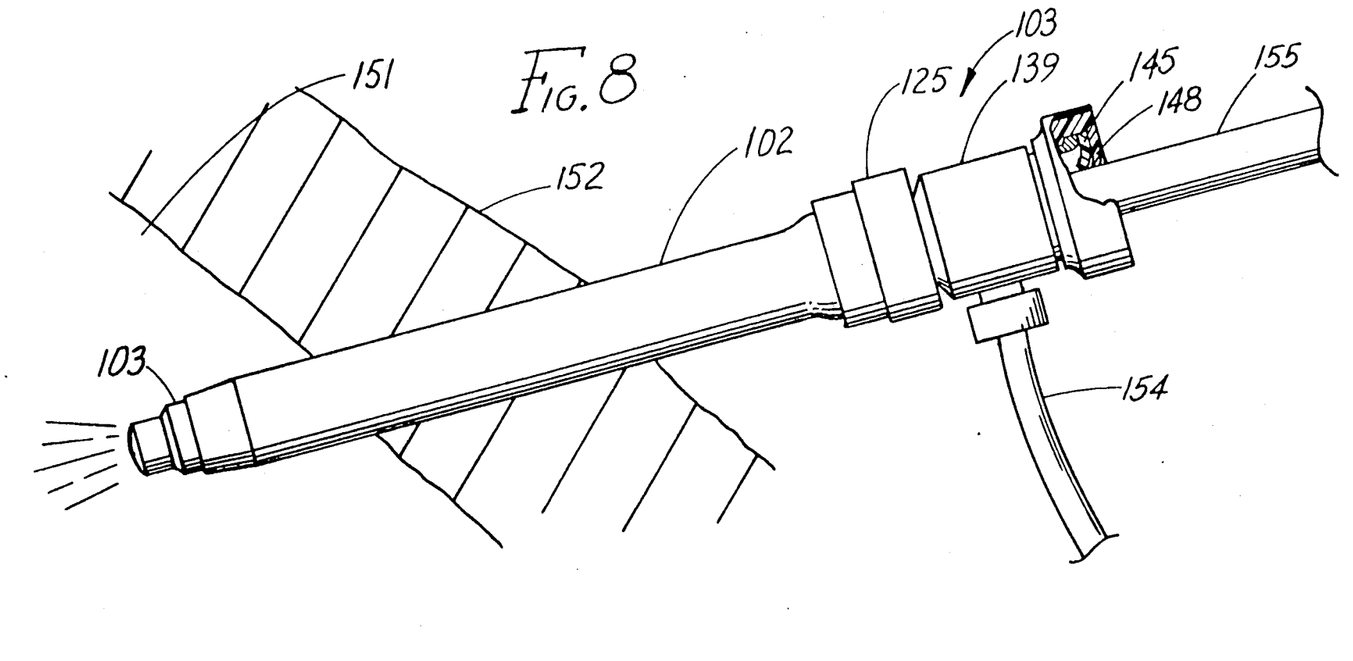

Depicted in FIGS. 6-8 is the method of percutaneously placing outer and inner access sheaths 102 and 103 into body cavity 151 through abdominal wall 152 with the use of wire guide 104 and dilator 101. The method comprises introducing wire guide 104 percutaneously into body cavity 151 through puncture site 153 as depicted in FIG. 6. Dilator 101 is positioned into the passageway of outer sheath 102 with shoulder 114 abutting against the proximal end of the outer sheath. The dilator and outer sheath are placed over wire guide 104 and inserted into the puncture site. Tapered distal end 106 dilates the puncture site as a force is applied to end cap 107 of the dilator. Saline is applied to wet hydrophilic material 105 coating the tapered distal end. The conically-shaped distal ends dilate the puncture site atraumatically to the diameter of the dilator and outer sheath.

Force is continually applied to end cap 107 to fully dilate puncture site 153 to the outer diameters of dilator 101 and sheath 102. When the dilator and the distal end of the outer sheath are positioned in body cavity 151 through the abdominal wall and puncture site, the dilator and wire guide are removed from the body cavity through the outer sheath.

After the wire guide and dilator are removed from the passageway of the outer sheath, inner sheath 103 is inserted through passageway 124 of outer sheath 102. The inner sheath is introduced into the body cavity by way of the outer sheath with seal 131 positioned at the proximal end of the outer sheath preventing the escape of insufflating gas from body cavity 151. Typically, a supply line 154 is attached to side port 144 of the inner sheath to supply the peritoneal body cavity with carbon dioxide gas for maintaining insufflation the body cavity.

When the inner sheath is fully inserted into the outer sheath, shoulder piece 139 abuts against the proximal end of outer sheath fitting 125 as depicted in FIG. 8. The distal end of the inner sheath will typically extend a short distance about the distal end of the outer sheath. When so positioned, seals 145 and 148 of the inner sheath along with the seal at the proximal end of outer sheath prevent the escape of insufflating gas from the body cavity. Insufflating gas line 154 also continues to supply insufflation gas to the peritoneal body cavity 151. As shown, endoscope 155 is introduced through the inner sheath through seals 145 and 148 into the peritoneal cavity for providing a viewing space through which the surgeon can view the cavity during a surgical procedure. One or more of these inner and outer access sheaths may be used to penetrate the peritoneal body cavity to permit the surgeon to introduce other endoscopic surgical instruments to perform a the particular procedure. The inner sheath may also be removed from the outer sheath to permit larger pieces of tissue or organs to be removed directly through the outer sheath.

Of course, it will be understood that the aforementioned medical device and method for endoscopic surgery is merely illustrative of the principles of this invention and that numerous other arrangements and methods may be devised by those skilled in the art without departing from the spirit and scope of the invention. In particular, it is contemplated that the outer sheath may also include a side port having one or more seals at its proximal end for cooperating with the dilator to insert the outer sheath into a body cavity. The dilator would be removed and endoscopic surgical instruments inserted solely through the outer sheath with the seals and insufflating line attached to the proximal end thereof. This medical device would also be inserted using a wire guide percutaneously inserted into the cavity. The outer diameter of a modified device is also contemplated to be smaller to provide for endoscopic instrument introduction. It is further contemplated that the dilator passageway opens at the proximal end of the elongated member or end cap.

What is claimed is:

1. A medical device for endoscopic surgery comprising:
   an elongated member having a tapered first distal end for dilating an entry site of a patient, a first proximal end, and an outside lateral wall extending between said first ends;
   a first passageway extending longitudinally in said member and opening from said tapered first distal end distally and from said outside lateral wall about said first proximal end; and
   an end cap positioned at said first proximal end and extending radially beyond said outside lateral wall of said elongated member for imparting force to said elongated member when dilating the entry site.

2. The medical device of claim 1 further comprising a hydrophilic material coating said tapered first distal end.

3. The medical device of claim 1 further comprising an outer sheath having a tapered second distal end, a second proximal end, and a second passageway extending longitudinally between said second ends and sized for positioning said elongated member therein.

4. The medical device of claim 3 wherein said outer sheath includes a fitting attached to said second proximal end, said fitting including a flexible seal having an aperture communicating with said second passageway and sized for sealing against said outside lateral wall of said member when said member is inserted through said aperture.

5. The medical device of claim 4 wherein said outside lateral wall includes a shoulder positioned about said first proximal end and sized for abutting against said second proximal end of said outer sheath, said first passageway opening laterally from said shoulder.

6. The medical device of claim 3 wherein said outer sheath includes a material having a slick surface.

7. The medical device of claim 3 further comprising a inner sheath having a third distal end, a third proximal end, and a third passageway extending longitudinally between said third ends, said inner sheath being sized for positioning within said second passageway of said outer sheath.

8. The medical device of claim 7 wherein said inner sheath further includes a shoulder positioned about said third proximal end and sized for abutting against said second proximal end of said outer sheath.

9. The medical device of claim 8 wherein said shoulder includes a side port communicating with said third passageway andextending laterally therefrom.

10. The medical device of claim 7 wherein said inner sheath includes a flexible seal attached about said third proximal end and having a slit communicating with said third passageway.

11. The medical device of claim 10 wherein said inner sheath comprises a second flexible seal attached about said third proximal end and having an aperture positioned adjacent said slit.

12. A medical device for endoscopic surgery comprising:
   a first elongated member having a tapered first distal end, a first proximal end, an outside lateral wall extending between said first ends, and a first passageway extending longitudinally between said first ends;
   a second elongated member positioned within said first passageway and having a second passageway opening from said tapered first distal end distally and from said outside lateral wall about said first proximal end; and
   an end cap attached at and extending from said first proximal end of said first elongated member.

13. The medical device of claim 12 further comprising a sleeve attached about said first proximal end of said first member and to said end cap and having a lateral opening communicating with said second passageway of said second member.

14. The medical device of claim 12 wherein said first member includes a hydrophilic material coating said first distal end.

15. The medical device of claim 12 further comprising a wire guide sized for passing through said second passageway of said second elongated member.

16. A medical device for endoscopic surgery, comprising:
    an outer sheath having a first distal end, a first proximal end, and a first hollow passageway extending longitudinally between said first ends; and
    an inner sheath having a second distal end, a second proximal end, a second hollow passageway extending longitudinally between said second ends, and a lateral opening positioned about said second proximal end and communicating with said second hollow passageway;
    said outer sheath including a first seal attached about said first proximal end and having an aperture sized for sealing around said inner sheath when said inner sheath is positioned within said first passageway of said outer sheath.

17. The medical device of claim 16 wherein said inner sheath includes a shoulder positioned about said second proximal end and sized for abutting against said first proximal end of said outer sheath.

18. The medical device of claim 17 wherein said inner sheath further includes a second seal positioned about said second proximal end and having a slit communicating with said second passageway.

19. The medical device of claim 18 wherein said inner sheath also includes a third seal positioned about said second proximal end and having an aperture communicating with said slit and sized for positioning surgical instruments therethrough.

20. The medical device of claim 16 further comprising a dilator having a conically-shaped third distal end, a third proximal end, an end cap attached to said third proximal end, and a third hollow passageway extending between said third ends and opening from said third distal end distally and from about said third proximal end laterally.

21. The medical device of claim 20 further comprising a wire guide sized for extending through said third passageway of said dilator.

22. A medical device for endoscopic surgery, comprising:
    a dilator including a first elongated member having a conically-shaped first distal end having a hydrophilic material coating, a first proximal end, an outside lateral wall extending between said first end, and a first passageway extending longitudinally therein; a second elongated member positioned within said first passageway and having a second distal end attached about said first distal end, a second proximal end attached to said lateral wall, and a second passageway opening from said distal ends distally and from said outside lateral wallabout said first proximal end; an end cap and a sleeve interconnecting said first proximal end and said end cap, said second passageway also opening through said sleeve;
    an outer sheath having a tapered third distal end, a third proximal end, and a third passageway extending longitudinally between said third ends and sized for positioning said dilator therein, said outer sheath also having a slick outer surface and a fitting attached about said third proximal end, said third passageway extending through said fitting, said fitting including a flexible seal having an aperture sized for sealing against said outside lateral wall when said dilator is inserted in said third passageway, said sleeve being sized for abutting against said third proximal end of said outer sheath;
    an inner sheath sized for positioning within said third passageway of said outer sheath and having a tapered fourth distal end, a fourth proximal end, a fourth passageway extending longitudinally between said fourth ends, and a shoulder positioned about said fourth proximal end and sized for abutting against said third proximal end of said outer sheath, said shoulder including an opening communicating with said fourth passageway and extending laterally therefrom, said inner sheath further including first and second flexible seals attached about said fourth proximal end, said first seal having a slit communicating with said fourth passageway, said second seal having an aperture therein positioned adjacent said slit; and
    a wire guide sized for extending through said second passageway of said dilator.

23. A method of percutaneously placing inner and outer access sheaths into a body cavity, comprising:
    introducing a wire guide percutaneously into said body cavity through a puncture site;
    dilating said puncture site with a dilator and said outer sheath placed over said wire guide;
    positioning said dilator and the distal end of said outer sheath into said body cavity through said dilated puncture site;
    removing said dilator and wire guide from said body cavity through said outer sheath; and
    introducing said inner sheath into said body cavity through said outer sheath when positioned in said cavity through said dilated puncture site.

24. The method of claim 23 wherein the step of dilating said puncture site includes wetting a hydrophilic material coating the conically-shaped distal end of said dilator and pushing an end cap at the proximal end of said dilator to introduce the conically-shaped distal end of said dilator into said puncture site.

25. The method of claim 24 further comprising insufflating said body cavity through a side port of said inner access sheath.

* * * * *